United States Patent
Kim et al.

(10) Patent No.: US 9,308,045 B2
(45) Date of Patent: *Apr. 12, 2016

(54) SYSTEM AND METHOD FOR PERFORMING AN ELECTROSURGICAL PROCEDURE USING AN ABLATION DEVICE WITH AN INTEGRATED IMAGING DEVICE

(71) Applicant: Vivant Medical, Inc., Boulder, CO (US)

(72) Inventors: Steven Kim, Los Altos, CA (US); Kyle R. Rick, Boulder, CO (US); Mani N. Prakash, Boulder, CO (US)

(73) Assignee: Covidien LP, Mansfield, MA (US)

( * ) Notice: Subject to any disclaimer, the term of this patent is extended or adjusted under 35 U.S.C. 154(b) by 296 days.

This patent is subject to a terminal disclaimer.

(21) Appl. No.: 13/681,741

(22) Filed: Nov. 20, 2012

(65) Prior Publication Data

US 2013/0079765 A1 Mar. 28, 2013

Related U.S. Application Data

(63) Continuation of application No. 12/696,966, filed on Jan. 29, 2010, now Pat. No. 8,313,486.

(51) Int. Cl.
| | | |
|---|---|---|
| *A61B 18/18* | (2006.01) | |
| *A61B 18/12* | (2006.01) | |
| *A61B 19/00* | (2006.01) | |
| *A61B 8/12* | (2006.01) | |

(52) U.S. Cl.
CPC ......... *A61B 18/1815* (2013.01); *A61B 18/1206* (2013.01); *A61B 18/18* (2013.01); *A61B 8/12* (2013.01); *A61B 19/5225* (2013.01); *A61B 2018/1869* (2013.01); *A61B 2019/5236* (2013.01); *A61B 2019/5276* (2013.01)

(58) Field of Classification Search
CPC .................... A61B 2018/1869; A61B 18/1815
USPC .................................................. 607/154, 156
See application file for complete search history.

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| 5,366,490 A | 11/1994 | Edwards et al. |
| 5,385,148 A | 1/1995 | Lesh et al. |

(Continued)

FOREIGN PATENT DOCUMENTS

| | | |
|---|---|---|
| DE | 390937 | 3/1924 |
| DE | 1099658 | 2/1961 |

(Continued)

OTHER PUBLICATIONS

U.S. Appl. No. 08/483,742, filed Jun. 7, 1995.

(Continued)

*Primary Examiner* — Jocelyn D Ram

(57) ABSTRACT

An ablation device includes an antenna assembly having a radiating portion configured to deliver energy from a power source to tissue. The radiating portion has an outer conductor and an inner conductor. The inner conductor is disposed within the outer conductor. The device also includes an imaging device operably coupled to the radiating portion. The imaging device is configured to generate imaging data corresponding to tissue proximate the radiating portion of the antenna assembly.

10 Claims, 4 Drawing Sheets

(56) References Cited

U.S. PATENT DOCUMENTS

| | | | |
|---|---|---|---|
| 5,409,006 | A | 4/1995 | Buchholtz et al. |
| 5,465,723 | A * | 11/1995 | Angelsen et al. ............. 600/448 |
| 5,507,743 | A * | 4/1996 | Edwards et al. ................ 606/41 |
| 5,536,240 | A | 7/1996 | Edwards et al. |
| 5,536,267 | A | 7/1996 | Edwards et al. |
| 5,558,672 | A | 9/1996 | Edwards et al. |
| 5,569,241 | A | 10/1996 | Edwards |
| 5,599,294 | A | 2/1997 | Edwards et al. |
| 5,599,345 | A | 2/1997 | Edwards et al. |
| 5,599,346 | A | 2/1997 | Edwards et al. |
| 5,861,002 | A | 1/1999 | Desai |
| 5,964,755 | A | 10/1999 | Edwards |
| D424,694 | S | 5/2000 | Tetzlaff et al. |
| D425,201 | S | 5/2000 | Tetzlaff et al. |
| 6,097,985 | A | 8/2000 | Kasevich et al. |
| 6,179,832 | B1 | 1/2001 | Jones et al. |
| 6,273,886 | B1 | 8/2001 | Edwards et al. |
| D449,886 | S | 10/2001 | Tetzlaff et al. |
| D457,958 | S | 5/2002 | Dycus et al. |
| D457,959 | S | 5/2002 | Tetzlaff et al. |
| 6,394,956 | B1 * | 5/2002 | Chandrasekaran et al. .. 600/439 |
| 6,419,653 | B2 | 7/2002 | Edwards et al. |
| 6,470,217 | B1 | 10/2002 | Fenn et al. |
| 6,477,426 | B1 | 11/2002 | Fenn et al. |
| 6,514,249 | B1 | 2/2003 | Maguire et al. |
| 6,569,159 | B1 | 5/2003 | Edwards et al. |
| 6,605,085 | B1 | 8/2003 | Edwards |
| 6,682,526 | B1 | 1/2004 | Jones et al. |
| 6,690,976 | B2 | 2/2004 | Fenn et al. |
| 6,725,095 | B2 | 4/2004 | Fenn et al. |
| 6,730,081 | B1 | 5/2004 | Desai |
| D496,997 | S | 10/2004 | Dycus et al. |
| D499,181 | S | 11/2004 | Dycus et al. |
| D525,361 | S | 7/2006 | Hushka |
| D531,311 | S | 10/2006 | Guerra et al. |
| D533,942 | S | 12/2006 | Kerr et al. |
| D535,027 | S | 1/2007 | James et al. |
| 7,197,363 | B2 * | 3/2007 | Prakash et al. ................ 607/156 |
| D541,418 | S | 4/2007 | Schechter et al. |
| D541,938 | S | 5/2007 | Kerr et al |
| 7,326,201 | B2 | 2/2008 | Fjield et al. |
| D564,662 | S | 3/2008 | Moses et al. |
| 7,479,141 | B2 | 1/2009 | Kleen et al. |
| 7,517,346 | B2 * | 4/2009 | Sloan et al. ..................... 606/41 |
| 7,822,460 | B2 | 10/2010 | Halperin et al. |
| 8,343,149 | B2 * | 1/2013 | Rossetto et al. ................ 606/50 |
| 2002/0026188 | A1 | 2/2002 | Balbierz et al. |
| 2004/0147917 | A1 | 7/2004 | Mueller |
| 2006/0106375 | A1 | 5/2006 | Werneth et al. |
| 2006/0241576 | A1 | 10/2006 | Diederich et al. |
| 2007/0167804 | A1 * | 7/2007 | Park et al. ..................... 600/459 |
| 2007/0198006 | A1 | 8/2007 | Prakash et al. |
| 2007/0255276 | A1 | 11/2007 | Sliwa, Jr. et al. |
| 2007/0265609 | A1 | 11/2007 | Thapliyal et al. |
| 2007/0265610 | A1 | 11/2007 | Thapliyal et al. |
| 2007/0293854 | A1 | 12/2007 | Pless et al. |
| 2007/0293855 | A1 | 12/2007 | Sliwa, Jr. et al. |
| 2008/0033493 | A1 * | 2/2008 | Deckman et al. ................. 607/3 |
| 2008/0058635 | A1 | 3/2008 | Halperin et al. |
| 2008/0120140 | A1 | 5/2008 | Sirohey et al. |
| 2008/0177138 | A1 | 7/2008 | Courtney et al. |
| 2008/0243162 | A1 | 10/2008 | Shibata et al. |
| 2008/0287801 | A1 | 11/2008 | Magnin |
| 2009/0036780 | A1 * | 2/2009 | Abraham ....................... 600/459 |
| 2009/0076375 | A1 | 3/2009 | Maschke |
| 2009/0088648 | A1 | 4/2009 | Jaffe et al. |
| 2009/0299360 | A1 * | 12/2009 | Ormsby ........................... 606/33 |
| 2010/0289891 | A1 | 11/2010 | Akiyama |
| 2013/0274658 | A1 | 10/2013 | Steinke et al. |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 0893101 | 1/1999 |
| EP | 1 159 926 | 5/2001 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2008142467 | 6/2008 |
| SU | 166452 | 11/1964 |
| SU | 401367 | 11/1974 |
| SU | 727201 | 4/1980 |
| WO | 0164121 | 9/2001 |
| WO | 03/088806 A2 | 10/2003 |
| WO | 2008144341 | 11/2008 |

(56) References Cited

OTHER PUBLICATIONS

U.S. Appl. No. 08/136,098, filed Oct. 14, 1993.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/251,857, filed Oct. 15, 2008.
U.S. Appl. No. 12/253,457, filed Oct. 17, 2008.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.
U.S. Appl. No. 12/619,462, filed Nov. 16, 2009.
U.S. Appl. No. 12/620,289, filed Nov. 17, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Scaling in Vaginal Hysterectomy" Obstetrics & Gynecology, vol. 102, No. 1, Jul. 2003.
B. Levy M.D. et al., "Update on Hysterectomy New Technologies and Techniques" OBG Management. Feb. 2003.
B. Levy M.D.. "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52. No. 3.
Chou, C.K., (1995) "Radiofrequency Hyperthermia in Cancer Therapy," Chapter 94In Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 1 0-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) l Vasc. Interv. Radiol, vol. 12, pp. 1021-1032.

(56) References Cited

OTHER PUBLICATIONS

Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994: pp. 729-731.
Heniford et al., "Initial Results with an Electrothermal Bipolar Vessel Sealer" Surgical Endoscopy (2001) 15:799-801.
Herman et al., "Laparoscopic Intestinal Resection With the LigaSure™ Vessel Sealing System: A Case Report" Innovations That Work, Feb. 2002.
Humphries Jr. et al., "Finite Element Codes to Model Electrical Heating and Non-L1near Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4: No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson, "Use of the LigaSurc™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1 st and 2nd Stage Orchiopexy" Innovations That Work, Nov. 2002.
Kennedy et al.. "High-burst-strength, feedback-controlled bipolar vessel scaling" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.

Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(2005•03): pp. 160-184.
Ogden, "Goertzel Alternative to the Fourier Transform" Jun. 1993 pp. 485-487 Electronics World: Reed Business Publishing, Sutton, Surrey, BG, vol. 99, No. 9, 1687.
Olsson M.D. el al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature: Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure. "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.

(56) References Cited

OTHER PUBLICATIONS

Urologix, Inc. Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09166708 dated Oct. 15, 2009.
European Search Report EP 09169376.2 extended dated Dec. 16, 2009.
European Search Report EP 09172838.6 extended dated Jan. 20, 2010.
European Search Report EP 09173268.5 extended dated Jan. 27, 2010.
International Search Report PCT/US98/18640 dated Jan. 29, 1998.
International Search Report PCT/US98/23950 dated Jan. 14, 1998.
International Search Report PCT/US99/24869 dated Feb. 11, 2000.

(56) References Cited

OTHER PUBLICATIONS

International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
European Search Report EP11000669 dated Jun. 30, 2011.
Partial European Search Report from Application No. 13003544.7 dated Sep. 19, 2013.
Published Japanese Application No. 2007-504910 (abstract only).
Japanese Office Action dated Jun. 14, 2014 in counterpart Japanese Application No. 2011-012862.
Japan Patent No. 3689135 (abstract included).
Japanese Patent Application Laid Open No. 09-94238 (abstract included).
Japanese Patent Application Laid Open No. 11-299803 (abstract included).
Japanese Office Action dated Feb. 19, 2016 in corresponding JP Application No. 2011-12862.

* cited by examiner

SYSTEM AND METHOD FOR PERFORMING AN ELECTROSURGICAL PROCEDURE USING AN ABLATION DEVICE WITH AN INTEGRATED IMAGING DEVICE

CROSS-REFERENCE TO RELATED APPLICATIONS

This present application is a Continuation of U.S. patent application Ser. No. 12/696,966 entitled "SYSTEM AND METHOD FOR PERFORMING AN ELECTROSURGICAL PROCEDURE USING AN ABLATION DEVICE WITH AN INTEGRATED IMAGING DEVICE" which was filed on Jan. 29, 2010, the entire contents of which are hereby incorporated by reference herein.

BACKGROUND

1. Technical Field

The present disclosure relates to energy-based apparatuses, systems and methods. More particularly, the present disclosure is directed to a system and method for performing an electrosurgical procedure using an ablation system including an integrated imaging device.

2. Background of Related Art

In the treatment of diseases such as cancer, certain types of cancer cells have been found to denature at elevated temperatures (which are slightly lower than temperatures normally injurious to healthy cells.) These types of treatments, known generally as hyperthermia therapy, typically utilize electromagnetic radiation to heat diseased cells to temperatures above 41° C., while maintaining adjacent healthy cells at lower temperatures where irreversible cell destruction will not occur. Other procedures utilizing electromagnetic radiation to heat tissue also include ablation and coagulation of the tissue. Such microwave ablation procedures, e.g., such as those performed for menorrhagia, are typically done to ablate and coagulate the targeted tissue to denature or kill the tissue. Many procedures and types of devices utilizing electromagnetic radiation therapy are known in the art. Such microwave therapy is typically used in the treatment of tissue and organs such as the prostate, heart, liver, lung, kidney, and breast.

One non-invasive procedure generally involves the treatment of tissue (e.g., a tumor) underlying the skin via the use of microwave energy. The microwave energy is able to non-invasively penetrate the skin to reach the underlying tissue. However, this non-invasive procedure may result in the unwanted heating of healthy tissue. Thus, the non-invasive use of microwave energy requires a great deal of control.

Presently, there are several types of microwave probes in use, e.g., monopole, dipole, and helical. One type is a monopole antenna probe, which consists of a single, elongated microwave conductor exposed at the end of the probe. The probe is typically surrounded by a dielectric sleeve. The second type of microwave probe commonly used is a dipole antenna, which consists of a coaxial construction having an inner conductor and an outer conductor with a dielectric junction separating a portion of the inner conductor. The inner conductor may be coupled to a portion corresponding to a first dipole radiating portion, and a portion of the outer conductor may be coupled to a second dipole radiating portion. The dipole radiating portions may be configured such that one radiating portion is located proximally of the dielectric junction, and the other portion is located distally of the dielectric junction. In the monopole and dipole antenna probe, microwave energy generally radiates perpendicularly from the axis of the conductor.

The typical microwave antenna has a long, thin inner conductor that extends along the axis of the probe and is surrounded by a dielectric material and is further surrounded by an outer conductor around the dielectric material such that the outer conductor also extends along the axis of the probe. In another variation of the probe that provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or combinations thereof.

Invasive procedures and devices have been developed in which a microwave antenna probe may be either inserted directly into a point of treatment via a normal body orifice or percutaneously inserted. Such invasive procedures and devices potentially provide better temperature control of the tissue being treated. Because of the small difference between the temperature required for denaturing malignant cells and the temperature injurious to healthy cells, a known heating pattern and predictable temperature control is important so that heating is confined to the tissue to be treated. For instance, hyperthermia treatment at the threshold temperature of about 41.5° C. generally has little effect on most malignant growth of cells. However, at slightly elevated temperatures above the approximate range of 43° C. to 45° C., thermal damage to most types of normal cells is routinely observed. Accordingly, great care must be taken not to exceed these temperatures in healthy tissue.

In the case of tissue ablation, a high radio frequency electrical current in the range of about 500 mHz to about 10 gHz is applied to a targeted tissue site to create an ablation volume, which may have a particular size and shape. The targeted tissue site is observed prior to the application of energy thereto to ensure accurate placement of the ablation device (e.g., microwave antenna) relative to the targeted tissue site. Typically, observation is facilitated through scanned data obtained through use of imaging devices such as CT, MRI, PET, or other tomographic or X-ray devices. However, images obtained using such scanning techniques before, during, or after an electrosurgical procedure, such as tissue ablation, are obtained from outside the patient and, therefore, are often lacking in quality due to distortions and the limitations of two-dimensional imaging.

SUMMARY

According to an embodiment of the present disclosure, an ablation device includes an antenna assembly having a radiating portion configured to deliver energy from a power source to tissue of a patient. The radiating portion has an outer conductor and an inner conductor. The inner conductor is disposed within the outer conductor. The device also includes an imaging device operably coupled to the inner conductor. The imaging device is configured to generate imaging data corresponding to tissue proximate the radiating portion of the antenna assembly.

According to another embodiment of the present disclosure, a microwave ablation system includes an antenna assembly configured to deliver energy from a power source to tissue of a patient and an introducer having a distal end configured to penetrate tissue. The introducer has a lumen disposed coaxially therein at least partially along its length.

The lumen is configured to receive the antenna assembly therein. The system also includes an imaging device disposed on the introducer configured to provide imaging data to a processing unit corresponding to tissue proximate the introducer. The processing unit is configured to generate an image based on the imaging data.

According to another embodiment of the present disclosure, a method for performing an electrosurgical procedure includes the steps of positioning an ablation device including an imaging device proximate a desired tissue site of a patient and imaging the desired tissue site to generate corresponding imaging data. The method also includes the steps of generating a display of the desired tissue site based on the imaging data and re-positioning the ablation device proximate the desired tissue site based on the display. The method also includes the step of supplying energy from an energy source to the ablation device for application to the desired tissue site.

BRIEF DESCRIPTION OF THE DRAWINGS

Various embodiments of the present disclosure are described herein with reference to the drawings wherein.

DETAILED DESCRIPTION

Figure 1:
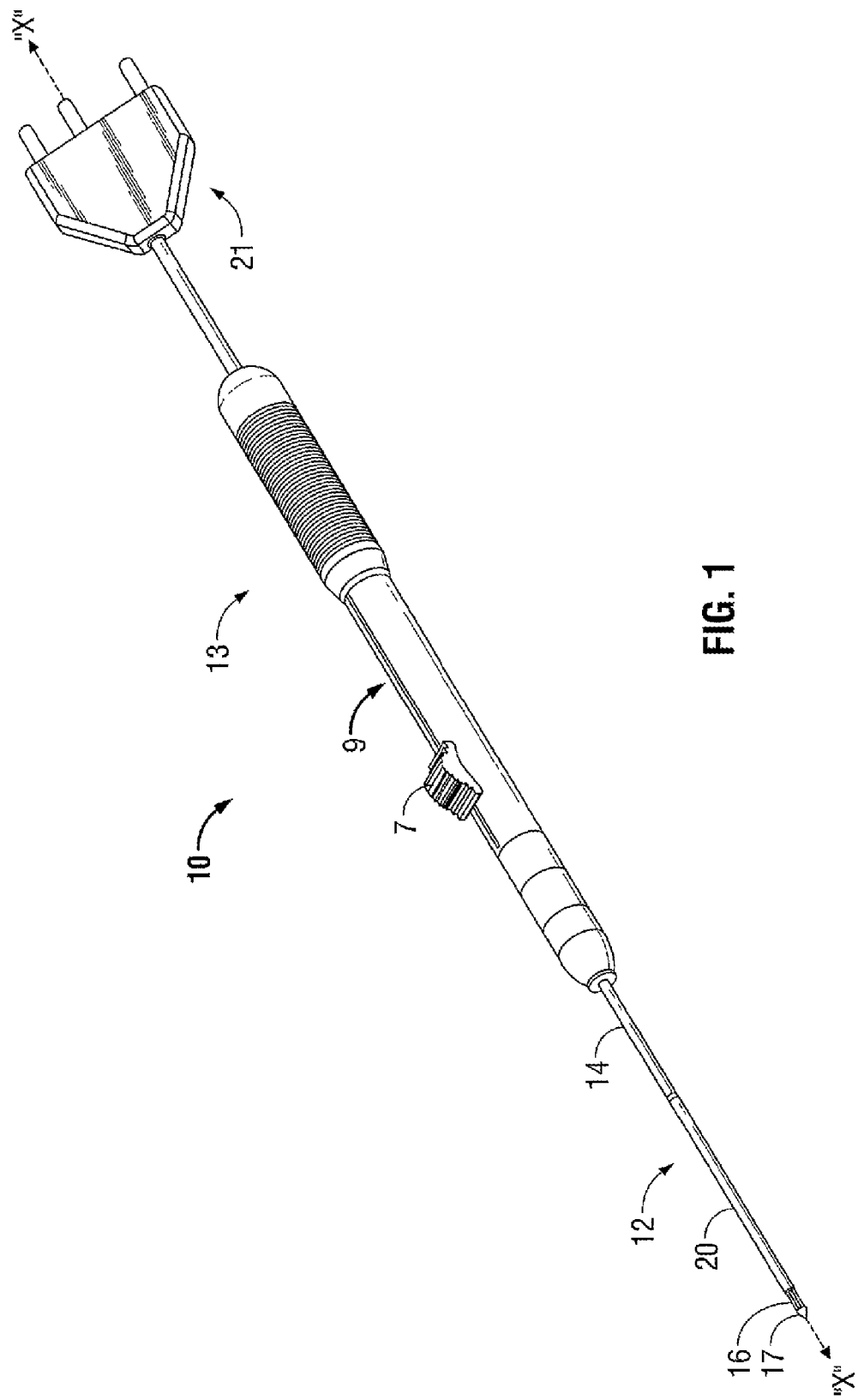
FIG. 1 is a perspective view of a microwave ablation device in accordance with an embodiment of the present disclosure.

Particular embodiments of the present disclosure are described hereinbelow with reference to the accompanying drawings. In the following description, well-known functions or constructions are not described in detail to avoid obscuring the present disclosure in unnecessary detail. In the discussion that follows, the term "proximal" will refer to the portion of a structure that is closer to a user, while the term "distal" will refer to the portion of the structure that is farther from the user.

Generally, the present disclosure relates to the use of an ablation device having an integrated imaging device, such as an ultrasound transducer adapted to generate image data by generating sound waves within the ultrasound frequency range toward a desired imaging site and subsequently receiving echoing of such sound waves from the desired imaging site. The ability to radially visualize target tissue before, during, and/or after an ablation procedure in three dimensions allows a user to accurately place the ablation device within the target tissue and, further, to monitor ablation progress.

An ablation device (e.g., a microwave ablation device) in accordance with the present disclosure is referred to in the figures as reference numeral 10. While a microwave ablation device is described herein, it is contemplated that the present disclosure may also be used in connection with other types of ablation devices and other instruments, such as introducers. Such ablation devices may include an antenna and/or an electrode.

Referring initially to FIG. 1, ablation device 10 includes an antenna 12 and a handle portion 13. Antenna 12 includes a shaft or feedline 14 having an inner conductor 16 and an outer conductor 20, which defines a longitudinal axis X-X. Outer conductor 20 may be, for example, an introducing structure (e.g., needle) configured to pierce and/or penetrate tissue. A power transmission cord 21 is shown and connects ablation device 10 to a suitable electrosurgical generator 22 (see FIGS. 2A and 2B). Additionally, an actuation element 7 is illustrated in FIG. 1 in accordance with various embodiments of the present disclosure. Actuation element 7 is operably coupled to inner conductor 16 and movable along a track 9 disposed at least partially along the length of handle portion 13 to move inner conductor 16 relative to outer conductor 20. More specifically, distal actuation of actuation element 7 along track 9 deploys or extends inner conductor 16 from outer conductor 20 and proximal actuation of actuation element 7 along track 9 retracts inner conductor 16 within outer conductor 20.

Figure 2A:
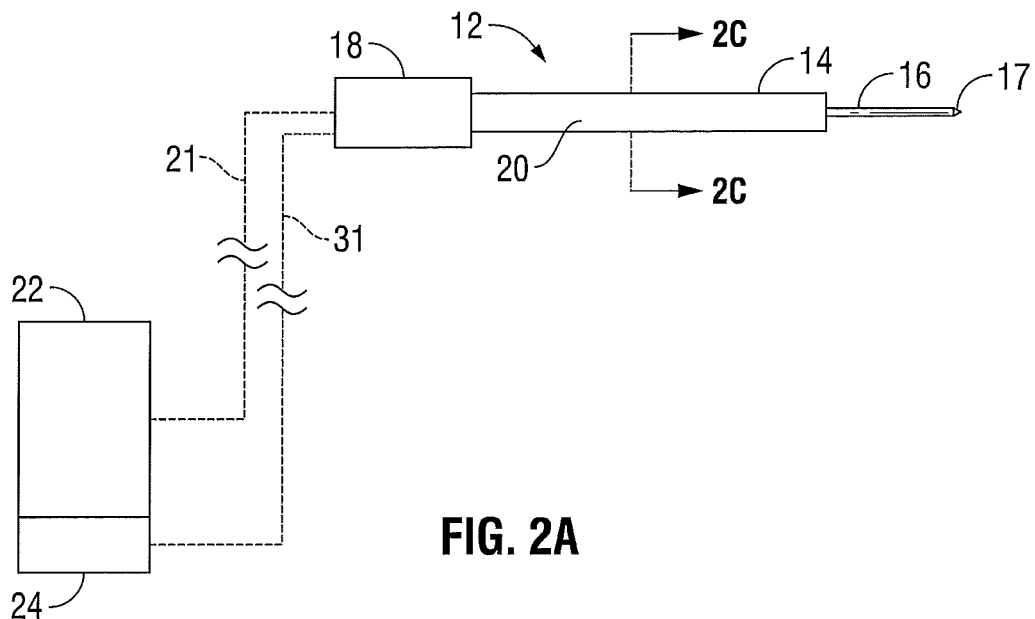
FIGS. 2A and 2B are schematic views of the microwave ablation device of FIG. 1 connected to a generator according to various embodiments of the present disclosure.
Figure 2B:
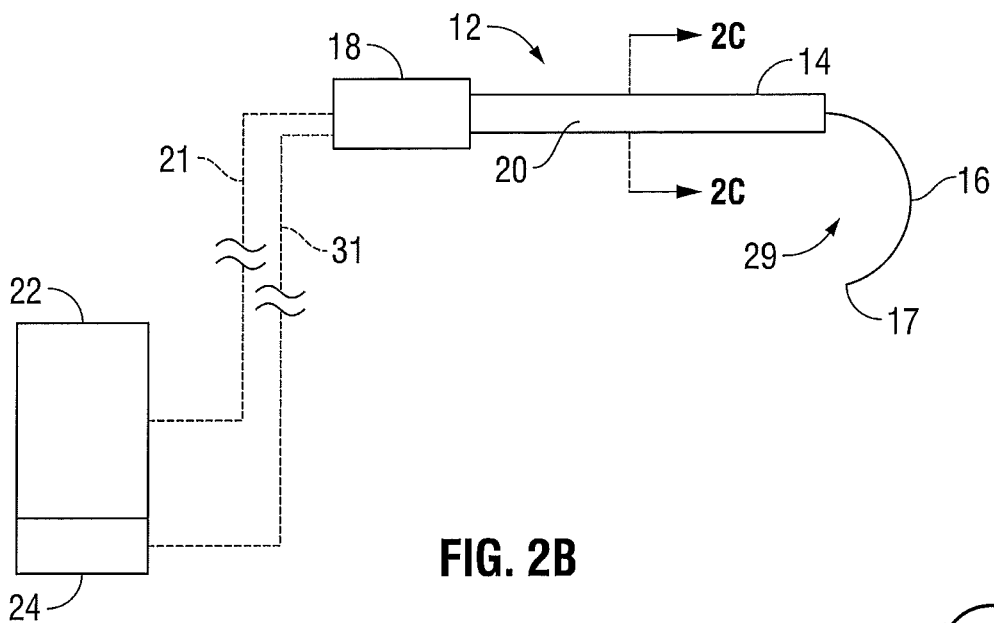

As seen in FIG. 2A, inner conductor 16 includes a distal tip 17 and is extendable from outer conductor 20. Several types of inner conductors 16 may be used in connection with the disclosed ablation device 10, including an inner conductor configured to deploy substantially in-line with outer conductor 20 (e.g., FIG. 2A) and an inner conductor configured to deploy in a curved orientation (e.g., FIG. 2B) along a curvilinear path to define an ablation region 29. In the illustrated embodiments of FIGS. 2A and 2B, a proximal end of feedline 14 includes a coupler 18 that electrically couples antenna 12 to generator 22 via power transmission cord 21.

In some embodiments, distal tip 17 allows for insertion of antenna 12 into tissue with minimal resistance. In those cases where the antenna 12 is inserted into a pre-existing opening, distal tip 17 may be rounded or flat.

Figure 2C:
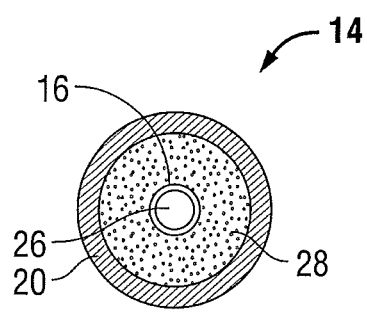
FIG. 2C is a cross-sectional view taken along section line 2C-2C of FIGS. 2A and 2B.

As shown in FIG. 2C, feedline 14 may be in the form of a coaxial cable. Portions of feedline 14 may be formed of outer conductor 20 surrounding inner conductor 16. Each of inner conductor 16 and/or outer conductor 20 may be made of a suitable conductive metal that may be semi-rigid or flexible, such as, for example, copper, gold, or other conductive metals with similar conductivity values. Alternatively, portions of each inner conductor 16 and outer conductor 20 may also be made from stainless steel that may additionally be plated with other materials, e.g., other conductive materials, to improve conductivity or decrease energy loss.

With continued reference to FIG. 2C, feedline 14 of antenna 12 is shown including a dielectric material 28 surrounding at least a portion of a length of inner conductor 16 and outer conductor 20 surrounding at least a portion of a length of dielectric material 28 and/or inner conductor 16. That is, dielectric material 28 is interposed between inner conductor 16 and outer conductor 20, to provide insulation therebetween and is comprised of any suitable dielectric material.

Figure 3A:
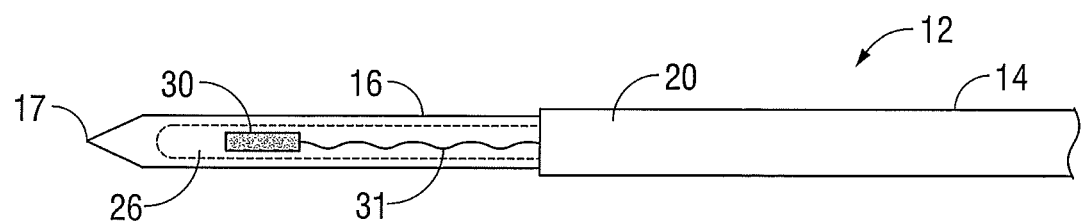
FIGS. 3A and 3B are enlarged side views of the microwave ablation device of FIG. 1 according to various embodiments of the present disclosure.
Figure 3B:
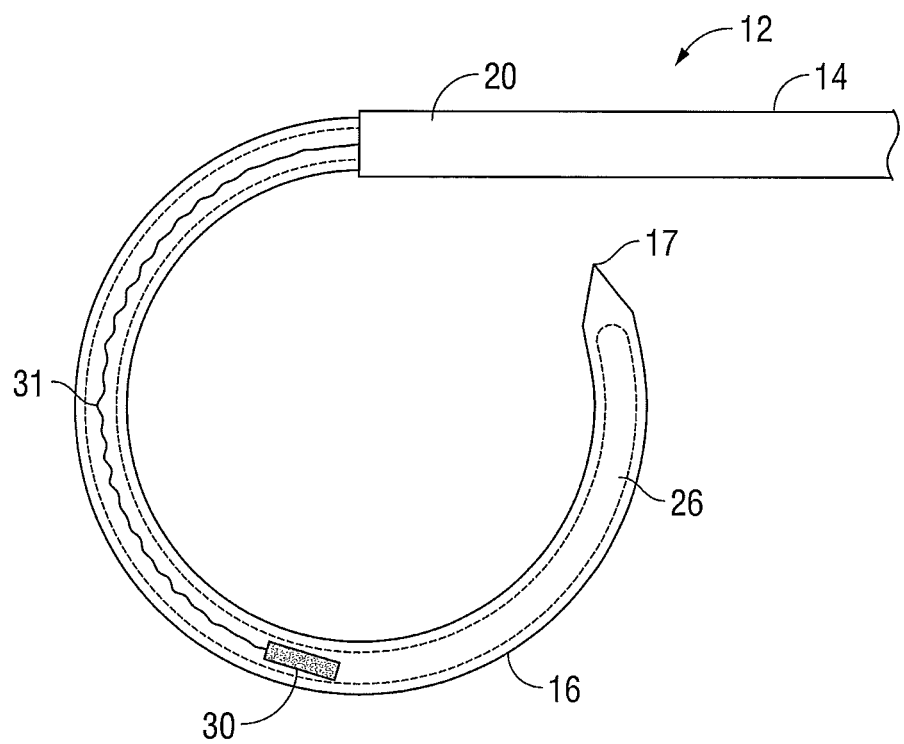

With reference to FIGS. 3A and 3B, antenna 12 may be embodied having a straight probe configuration of radiating portion 12, as shown in FIG. 3A, or a loop probe configuration of radiating portion 12, as shown in FIG. 3B. In either scenario, radiating portion 12 includes a lumen 26 defined coaxially therethrough and at least partially along the length thereof. Disposed within lumen 26 is an imaging device 30 adapted to image a desired ablation area. An electrical lead 31 electrically connects imaging device 30 to a processing unit 24 configured to process data generated by imaging device 30 for representation on a display (see, e.g., FIGS. 2A, 2B). Although not shown entirely in the accompanying figures, lead 31 is connected to processing unit 24 and extends therefrom through handle assembly 13 and lumen 26 to connect to imaging device 30. Processing unit 24 may include a processor operably coupled with a memory (not shown) that stores suitable image processing software executable as programmable instructions by the processor to cause processing unit 24 to generate an image based on imaging data received from imaging device 30. Processing unit 24 may be a stand-alone device or may be incorporated within generator 22. Imaging device 30 may be, for example, an ultrasound transducer adapted to generate and receive sound waves to generate imaging data corresponding to the tissue area surrounding radiating portion 12. In other embodiments, imaging device 30 may be, for example, a CAT scan device, a PET scan device, an X-ray device, an MRI device, or other tomographic or X-ray device utilized to generate imaging data corresponding to the desired ablation area.

Imaging device 30 may be fixedly mounted within lumen 26 (e.g., via adhesive, fastener, etc.) or may be slidably disposed within lumen 26 such that imaging device 30 may be moved proximally and distally within lumen 26 and/or rotated about longitudinal axis X-X of radiating portion 12 to facilitate 360 degree and/or radial imaging of surrounding tissue along the entire length of inner conductor 16. This configuration of imaging device 30 makes three-dimensional imaging of the desired tissue site possible. With this purpose in mind, ablation device 10 may also by rotated 360 degrees by the user to achieve three-dimensional imaging of the desired tissue site.

Figure 4A:
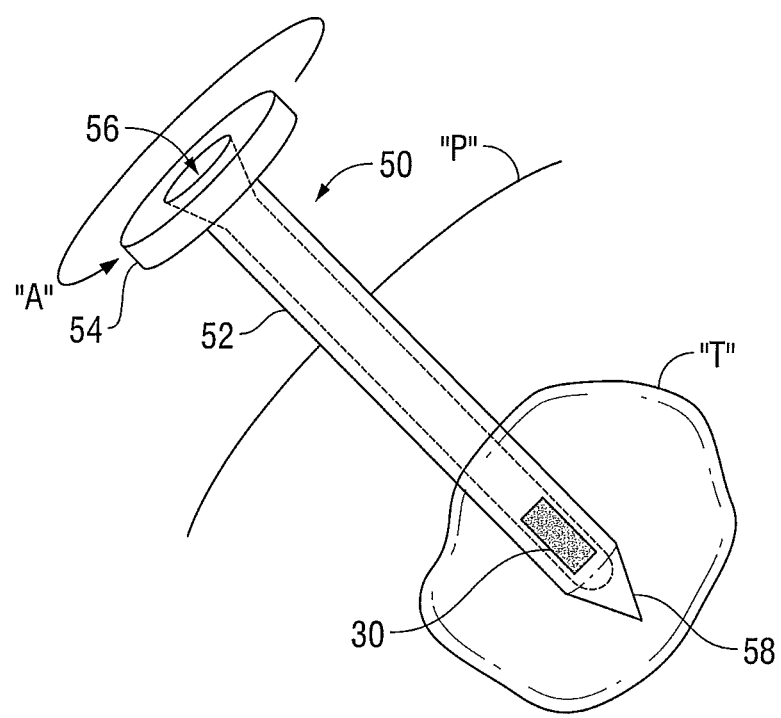
FIGS. 4A and 4B are perspective views of an introducer for use with the microwave ablation device of FIG. 1.
Figure 4B:
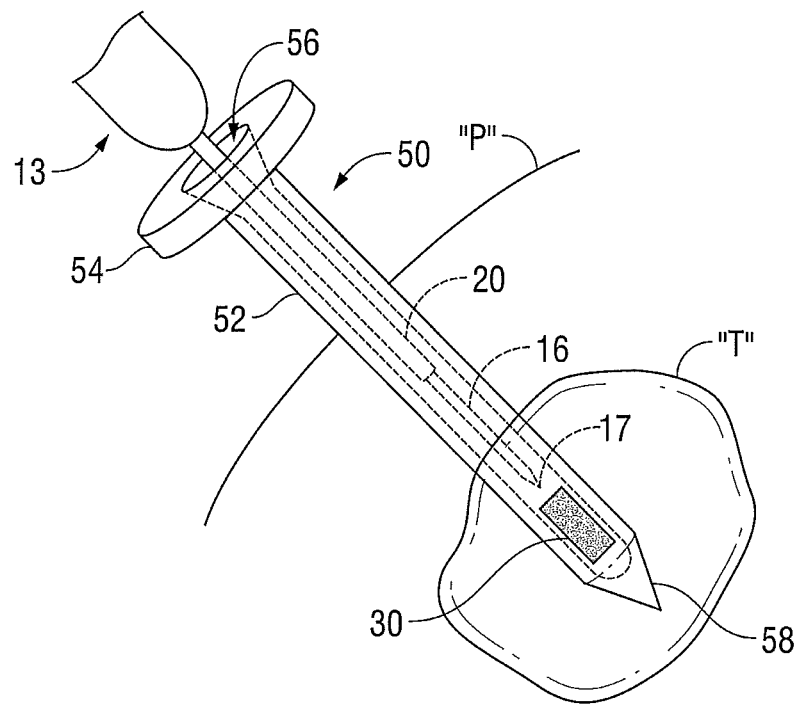

In another embodiment shown in FIGS. 4A and 4B, imaging device 30 may be used in conjunction with an introducer 50 to facilitate placement of radiating portion 12 relative to an ablation area or a tumor "T". Introducer 50 includes a shaft 52 extending from a proximal hub 54 to a distal end 58, and a lumen 56 disposed coaxially through shaft 52 from proximal hub 54 distally toward distal end 58 through at least a portion of the length of shaft 52. Distal end 58 may be tapered to allow for insertion of introducer 50 into tissue with minimal resistance. Shaft 52 is inserted into tissue of a patient "P" until distal portion 58 of shaft 52 is positioned adjacent to or within an ablation area of tissue, e.g., tumor "T", as shown in FIGS. 4A and 4B. Imaging device 30 is utilized to image the area surrounding distal portion 58 of shaft 52 to ensure that introducer 50 is properly placed relative to the ablation area. More specifically, imaging data relating to the ablation area is received and processed by processing unit 24 for viewing by the surgeon. Based on the generated imaging data, the user may maneuver or re-position the introducer 50 within the patient "P", if necessary, to ensure accurate position of distal portion 58 of shaft 52 relative to tumor "T" before ablation thereof. As illustrated by rotational arrow "A" of FIG. 4A, introducer 50 may be rotated about the longitudinal axis of shaft 52 such that imaging device 30 may be rotated 360 degrees to completely image the ablation area.

Once introducer 50 is desirably positioned, ablation device 10 may then be inserted within lumen 56 while maintaining the position and orientation of shaft 52 within patient "P". Ablation device 10 is advanced distally within lumen 56 such that radiating portion 12 of device 10 is adjacent to or within tumor "T". The length of radiating portion 12 may be configured to fit within shaft 52 such that a proximal end of handle portion 13 and proximal hub 54 contact one another in a lock-fit manner (not explicitly shown). During and/or after an ablation procedure, the ablation area may be imaged to enable the user to monitor the progress and/or completeness of the ablation.

In the illustrated embodiment of FIGS. 4A and 4B, imaging device 30 is shown without electrical lead 31 to illustrate that imaging device 30 may be configured to communicate imaging data to processing unit 24 wirelessly from within patient "P". As such, an electrical lead (e.g., lead 31) connecting imaging device 30 to processing unit 24 may not be necessary to effect proper and intended implementation of any of the embodiments disclosed herein.

In use, energy (e.g., microwave energy) generated by generator 22 in close proximity to imaging device 30 may cause interference with image data generated by imaging device 30 during an imaging procedure. In this scenario, imaging device 30 and generator 22 may be configured, in certain embodiments, to automatically operate in mutual exclusion relative to one another. More specifically, generator 22 continuously receives and processes an imaging signal generated by imaging device 30 (e.g., wirelessly) and/or processing unit 24 that continuously indicates in real-time whether or not an imaging procedure is currently being performed by imaging device 30. Based on the generated signal, generator 22 terminates energy output during an imaging procedure and continues energy output while no imaging procedure is being performed by the imaging device 30. In this manner, imaging procedures and electrosurgical procedures (e.g., microwave ablation) may be performed in close proximity and essentially during the same procedure or operation without adverse effects (e.g., image distortion) to the imaging process caused by interference from the output of generator 22.

Those skilled in the art will appreciate that imaging device 30 and/or processing unit 24 include suitable circuitry (e.g., processor, memory, a/d converter, etc.) configured to generate the imaging signal as output and, further, that generator 22 includes suitable circuitry configured to receive and process the imaging signal as input. In some embodiments, processing unit 24 and/or ablation device 10 may include buttons, switches, actuators, or the like, configured to activate or deactivate imaging device 30 and/or to generate a signal to generator 22 indicating the activation, suspension, and/or termination of an imaging procedure.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. For example, it should be understood that any of the above disclosed embodiments may be configured such that imaging device 30 generates a logic low to indicate an imaging procedure is currently being performed and, vice-versa, a logic high may indicate that no imaging procedure is currently being performed. Those skilled in the art will envision other modifications within the scope and spirit of the claims appended hereto.

What is claimed is:

1. An ablation device, comprising:
   an antenna assembly having a handle portion and an elongated radiating portion extending from the handle portion, the radiating portion configured to deliver energy from a power source to tissue and including outer and inner conductors extending therethrough, the inner conductor disposed within the outer conductor; and
   an imaging device disposed within a lumen defined coaxially through at least a portion of the radiating portion, the imaging device configured to generate imaging data corresponding to the tissue and to be movable within the lumen.

2. An ablation device according to claim 1, wherein the inner conductor is configured to deploy from the outer conductor into the tissue.

3. An ablation device according to claim 1, wherein the imaging device is selected from the group consisting of ultrasound transducers, CAT scan devices, MRI devices, and PET scan devices.

4. An ablation device according to claim 1, wherein the imaging device is rotatable relative to the radiating portion and configured to generate three-dimensional image data of tissue surrounding the radiating portion.

5. An ablation device according to claim 1, wherein the imaging device is configured to communicate the imaging data to a processing unit adapted to generate a display based on the imaging data.

6. An ablation device according to claim 5, wherein the imaging device is configured to communicate the imaging data to the processing unit wirelessly.

7. An ablation device according to claim 1, wherein the antenna assembly includes a straight probe configuration.

8. An ablation device according to claim 1, wherein the antenna assembly includes a loop probe configuration configured to deploy in a curvilinear path to define an ablation area.

9. An ablation device according to claim 1, wherein the lumen is defined coaxially through at least a portion of the inner conductor.

10. An ablation device, comprising:

an antenna assembly having a radiating portion configured to deliver energy from a power source to tissue of a patient, wherein the radiating portion includes an outer conductor and an inner conductor extending therethrough, the inner conductor coaxially defining a lumen at least partially therethrough and configured for selective deployment from the outer conductor into tissue; and an imaging device disposed within the lumen and configured to generate imaging data corresponding to the tissue, wherein the imaging device is movable within the lumen.

* * * * *